(12) United States Patent
Briglin et al.

(10) Patent No.: US 12,203,887 B2
(45) Date of Patent: Jan. 21, 2025

(54) PARTIAL PRESSURE GAUGE ASSEMBLY FOR PROCESS CONTAMINANT DETECTION USING PHOTOIONIZATION AND ASSOCIATED METHOD

(71) Applicants: NAIL ALLIANCE, LLC, Gladstone, MO (US); COSMEX CO., LTD, New Taipei (TW)

(72) Inventors: Shawn M. Briglin, Cazenovia, NY (US); Michael F. Vollero, Manlius, NY (US); John Gordon Wiley, Marietta, NY (US)

(73) Assignee: INFICON, INC., East Syracuse, NY (US)

( * ) Notice: Subject to any disclaimer, the term of this patent is extended or adjusted under 35 U.S.C. 154(b) by 0 days.

(21) Appl. No.: 18/286,627

(22) PCT Filed: Apr. 21, 2023

(86) PCT No.: PCT/US2023/019401
§ 371 (c)(1),
(2) Date: Oct. 12, 2023

(87) PCT Pub. No.: WO2023/205417
PCT Pub. Date: Oct. 26, 2023

(65) Prior Publication Data
US 2024/0085374 A1 Mar. 14, 2024

Related U.S. Application Data

(60) Provisional application No. 63/332,351, filed on Apr. 19, 2022.

(51) Int. Cl.
G01N 27/66 (2006.01)
G01N 33/00 (2006.01)
H01J 41/06 (2006.01)

(52) U.S. Cl.
CPC ......... *G01N 27/66* (2013.01); *G01N 33/0027* (2013.01); *H01J 41/06* (2013.01)

(58) Field of Classification Search
CPC ...... H01J 41/06; G01N 27/66; G01N 33/0027
See application file for complete search history.

(56) References Cited

U.S. PATENT DOCUMENTS 2,961,601 A * 11/1960 Baughman ............. H04J 41/04
315/108
3,341,727 A * 9/1967 Schuemann ............ H01J 41/04
315/108

(Continued)

OTHER PUBLICATIONS

The International Bureau of WIPO; International Preliminary Report on Patentability; International Application No. PCT/US2023/019041; Dated: Oct. 8, 2024; 7 pages.

*Primary Examiner* — Jeff W Natalini
(74) *Attorney, Agent, or Firm* — Barclay Damon LLP

(57) ABSTRACT

A photoionization sensor assembly includes a housing defining a chamber with a first end and an opposing second end and being permeable to the analyte gas and non-analyte gases. A radiation source is structured to emit photons into the chamber. A first, second and third electrode are positioned in the chamber. The photons ionize the analyte gas, are insufficient to ionize the non-analyte gases, and causing ejection of photoelectrons from the third electrode. A controller is structured to receive a measurement of a total pressure and electrically bias the electrodes to collect the photoelectrons on the first and second electrodes in a ratio dependent on the total pressure. The controller is structured to determine the ratio of photoelectrons that are collected on the first and second electrodes at the total pressure and determine an amount of electrical current due to ionization by correcting the measured current using the determined ratio.

26 Claims, 11 Drawing Sheets

(56) References Cited

U.S. PATENT DOCUMENTS

| | | | |
|---|---|---|---|
| 4,398,152 A | | 8/1983 | Leveson |
| 6,313,638 B1 * | | 11/2001 | Sun .................. H01J 41/02 |
| | | | 324/464 |
| 2007/0144904 A1 | | 6/2007 | Strohmaier et al. |
| 2007/0189359 A1 | | 8/2007 | Chen et al. |
| 2016/0362787 A1 | | 12/2016 | Vollero et al. |
| 2017/0254714 A1 * | | 9/2017 | Yoshida .................. G01N 27/62 |

* cited by examiner

PARTIAL PRESSURE GAUGE ASSEMBLY FOR PROCESS CONTAMINANT DETECTION USING PHOTOIONIZATION AND ASSOCIATED METHOD

CROSS-REFERENCE TO RELATED APPLICATION

This application is a national stage application pursuant to 35 U.S.C. § 371 of International Application No. PCT/US2023/019041, filed on Apr. 19, 2023, which claims priority to, and the benefit of, U.S. Provisional Patent Application Ser. No. 63/332,351, filed Apr. 19, 2022, and entitled "PARTIAL PRESSURE GAUGE FOR PROCESS CONTAMINANT DETECTION USING PHOTOIONIZATION." The entirety of which is incorporated herein by reference.

TECHNOLOGICAL FIELD

The disclosed invention relates generally to the field of pressure gauges, and specifically to partial pressure gauges for use in fault detection on semiconductor process tools where the gauge makes use of high energy photons for the selective measurement of contaminants in a reduced pressure of an inert gas.

BACKGROUND

Modern integrated circuit (IC) fabrication begins with high purity semiconductor wafers and then these wafers proceed through hundreds of tightly controlled process steps over a period of weeks or months. After the wafer completes these steps it is diced into a large number of smaller dies. These dies are then packaged and the resulting devices, such as ICs, find a home at the heart of many modern electronics devices. Producing high performance semiconductor devices with high yield requires tight control of the micro environments surrounding the wafers. At various production steps, the partially completed devices are at more or less risk from damage as a result of exposure to certain process contaminants. For one example, trace oxygen exposure during the growth of the metallic layers involved in contacting the source or drain regions of the transistor can increase the electrical resistance of this layer and degrade device time constants, thus lowering yield. As a second example, trace hydrocarbon contaminants residual to the wafer surface can degrade components of the semiconductor processing tool, such as lithographic optics. As a third example, precursor chemicals used in metallization of dielectric deposition can be incompletely purged from the chamber or can leak from a process chamber back into a transfer chamber where they would damage transferring wafers. Thus it is important to monitor for these contaminants during steps of handling, storage, and the processing steps of the semiconductor wafers.

Typically the wafer's micro environments are maintained to be ultra clean from contaminants, and although some processes are at high vacuum (i.e., less than 1e-5 Torr), many modern semiconductor processes occur in a flow of inert gases at a much lower vacuum (1 to 100 Torr). This means that there are quite typically inert gases like Nitrogen, Argon, or Hydrogen present at high levels during process steps. Measuring the total pressure indicates the level of these major species, but it does not provide an acceptable indication of the trace contaminants that may be present at levels 1 million times lower. If for example, a 1 ppm level of oxygen was identified in a particular tool step, processing additional wafers can be suspended and the faulty component, such as a chamber o-ring, can be replaced to prevent additional wafer scrap and reduce tool down time. Similarly, small levels of organic contaminants on the wafer surface can cause defects in pattern transfer leading to edge placement error and other yield impactors. Beyond yield impacts, hydrocarbon contaminants can also leave the wafer surface degrading the complex and expensive lithographic components necessary in the latest semiconductor nodes. Replacing optics and masks damaged in this way can be extremely expensive. All of these yield and tool impactors are important to control in the highly competitive industry of semiconductor manufacturing. Besides contamination, there are other instances when it is important to determine trace level species in a background gas such as determining the endpoint of an etch.

Total pressure can be measured with a number of gauge types. These include Bayard-Alpert style ionization gauges, capacitance manometers, and thermocouple gauges among others. Formally, only the manometer measures the true pressure of the gas as the others provide an estimate of number density related to the ionization cross section, thermal transport, or other properties of the gas. However, it approximates to say that the most common types of gauges measure a property of the gas related to the gases total pressure rather than trace components.

This problem of measuring trace components has traditionally been solved by using a special type of "ion gauge" referred to as residual gas analyzers (RGA, e.g., a type of mass spectrometer). Like an ion gauge such as a Bayard-Alpert gauge, the RGA uses a high energy electron beam to convert neutral species into ions. At typical electron energies of 70 to 100 eV, all gas molecules can be ionized with some probability. The RGA includes a mass filter to separate these ions by differing mass to charge ratios (m/z). Associating m/z with the different gases present in the microenvironment, and combined with ionization cross-sections, and sensor m/z sensitivity factors can be used to estimate the partial pressure of different contaminating molecules even if these are present at low levels (i.e., 1 ppm) in a majority gas. Unfortunately, the use of mass spectrometry is not directly applicable to modern semiconductor processes operating at pressures from 1 to 100 Torr. This is because a low pressure (<1e-4 Torr) is necessary for operation of most RGAs. Briefly, in an RGA, low pressure is necessary for operation of the filament (cathode). At pressures >1e-4 Torr, space charge begins to mask the filament from its extraction fields. Additionally, ion bombardment and oxidation can erode the filament materials. Another issue with the RGA, is that low pressure is necessary to limit the effects of ion molecule collisions in the mass analyzer and to avoid ion feedback or plasma discharges in secondary electron amplifiers. Therefore, additional pumping is required in order to attach an RGA to many modern semiconductor tools or process steps. This adds costs, delays in response time, and requires substantial space around what is an already crowded semiconductor reactor chamber. It is also expensive. A need remains to measure the partial pressure of trace contaminants in these higher pressure micro environments.

An additional problem exists for gauges designed to operate at higher pressures (above about 1 Torr). In this pressure range, the mean free path of gas molecules is typically very short relative to the dimensions of the sensor. A change in total pressure can be detected quickly as the pressure front propagates at the speed of sound. However, determining the partial pressure of a minor species at a particular point of the chamber depends on the diffusion or transport of that species to the gauge. A partial pressure gauge must therefore be locatable close to the region of interest; otherwise, the sensor will not respond quickly enough to address many common problems in the semiconductor industry. In certain cases of gases flowing at high rates, a gauge may miss the leak or contaminant entirely because the contaminant is diluted by the time that it reaches a sensor installed on for example the foreline. Moreover, given that the space around a semiconductor tool is very limited, it is important to design a sensor that can be in close communication to areas of concern.

These are just some of the problems associated with total pressure gauges and conventional partial pressure gauges such as RGAs.

BRIEF SUMMARY

The current disclosure is directed to a sensor gauge assembly that can be inserted directly into the process environment. An embodiment of a partial pressure ion gauge comprises an electrical feedthrough flange, a plasma generating envelope, and a series of electrodes. A dielectric housing supports the ion and electron lenses and contains the plasma generation envelope fully inside the process environment.

Rather than use a hot cathode filament for ionization as is typical for the RGA discussed above, the sensor disclosed herein makes use of a lamp comprised of a self-contained plasma to generate high energy photons. The plasma envelope contains a sample of krypton gas at reduced pressure, although it could also contain argon, xenon, or other gases. A high electric field generated between two electrodes patterned onto the outside of the plasma envelope or otherwise located near to the envelope couple energy into contained gas and thus create the plasma which emits light as the excited plasma species relax back to their lower energy states. The envelope can be any dielectric that can be hermetically sealed and that can withstand the pressure differential between the plasma and the process. For example, it can be a molded piece of alumina. But most typically the plasma source is constructed from a blown piece of Pyrex® glass. Regardless of the material containing the plasma source, on one face of this lamp, there is a UV transparent crystal. This crystal is composed of a material that is transparent to high energy photons. In various embodiments the crystal may be comprised of magnesium fluoride, calcium fluoride, or lithium fluoride or some other suitable material. And as is well known from conventional photoionization sensors designed for operation in high pressure environments (e.g., atmospheric pressure), the ionization can be selective. In general, the photon energy of a krypton discharge has energy above the first ionization energy of most organic molecules, but not sufficient to ionize nitrogen or argon or hydrogen.

An embodiment of a gas sensor comprises this gas envelope on the inside of a flange. This gas envelope may be comprised of alumina. In an embodiment, the optical element comprises sapphire.

An embodiment of a sensor assembly for measuring a total pressure of a gas includes a housing defining a chamber including a first end and an opposing second end. The chamber is permeable to molecules of the gas surrounding the housing. A radiation source is structured to emit photons into the chamber. A first electrode is positioned towards the first end of the chamber, a second electrode is positioned in the chamber and a third electrode is positioned towards the second end of the chamber. A controller is in communication with at least the first and second electrodes. The photons emitted into the chamber cause an ejection of photoelectrons from the third electrode. The controller is structured to electrically bias the first, second and third conductors such that the ejected photoelectrons are attracted toward and collected on the first and second electrodes in a ratio that is dependent on a total pressure of the gas, wherein the photoelectrons generate an electrical current on the first and second electrodes. The controller is further structured to measure the electrical current generated on the first and second electrodes and determine the total pressure of the gas based on the electrical current generated on the first and second electrodes.

In an embodiment, the radiation source is positioned towards the first end of the chamber. In an embodiment, the second end of the chamber is at least partially open to a surrounding environment. In an embodiment, the third electrode comprises gold. In an embodiment, the radiation source is at least partially surrounded by the housing. In another embodiment, a ratio of a distance between the first and second electrodes to that of a distance between the second and third electrodes is about 8:1. In a further embodiment, at least one of the first, second and third electrodes comprises a grid.

An embodiment of a photoionization sensor assembly structured to measure an analyte gas in a presence of non-analyte gases includes a housing defining a chamber with a first end and an opposing second end. The chamber is permeable to molecules of the analyte gas and non-analyte gases surrounding the housing. A radiation source is structured to emit photons into the chamber. A first conductive electrode is positioned towards the first end of the chamber, a second conductive electrode is positioned in the chamber and a third conductive electrode is positioned towards the second end of the chamber. A controller is in communication with at least the first and second conductive electrodes. The emitted photons ionize at least some molecules of the analyte gas and are insufficient to ionize molecules of the non-analyte gases. The emitted photons further strike the third conductive electrode resulting in ejection of photoelectrons. The controller is structured to receive a measurement of a total pressure of the analyte gas and the non-analyte gases and electrically bias the first, second and third conductive electrodes such that the photoelectrons are attracted toward and collected on the first and second conductive electrodes in a ratio that is dependent on the total pressure of the analyte gas and the non-analyte gases. The controller is further structured to measure an electrical current generated on the first and second conductive electrodes and determine the ratio of the ejected photoelectrons that are collected on the first and second conductive electrodes at the total pressure. The controller is further structured to determine an amount of electrical current due to ionization of the analyte gas by correcting the measured current using the determined ratio to subtract an electrical current caused by the photoelectrons from the measured electrical current.

In an embodiment, the correcting of the measured current further comprises subtracting a fraction of the electrical current measured on the second conductive electrode from the electrical current measured on the first conductive electrode. In an embodiment, the photoionization sensor assembly further includes a pressure gauge mounted on a flange and structured to measure a total pressure and provide the measured total pressure to the controller. In an embodiment, the second end of the chamber is at least partially open to a surrounding environment. In an embodiment, the third conductive electrode comprises gold. In an embodiment, the radiation source is at least partially surrounded by the housing. In an embodiment, the radiation source is located at the first end of the chamber.

An embodiment of a method for measuring an analyte gas in a presence of non-analyte gases includes structuring a photoionization sensor to include:
(1) a housing defining a chamber with a first end and an opposing second end, wherein the chamber is permeable to molecules of the analyte gas and non-analyte gas surrounding the housing;
(2) a radiation source configured to emit photons;
(3) a first conductive electrode positioned towards the first end of the chamber;
(4) a second conductive electrode positioned in the chamber.
(5) a third conductive electrode positioned towards the second end of the chamber; and
(6) a controller in communication with at least the first and second conductive electrode.

The method further includes emitting photons from the radiation source into the chamber to ionize at least some molecules of the analyte gas, wherein the emitted photons are insufficient to ionize molecules of the non-analyte gases. The photons emitted from the radiation source into the chamber further strike the third conductive electrode and cause an ejection of photoelectrons.

The controller is structured receive a measurement of a total pressure of the analyte gas and the non-analyte gases and electrically bias the first, second and third conductive electrodes such that the photoelectrons are attracted toward and collected on the first and second conductive electrodes in a ratio that is dependent on the total pressure of the analyte gas and the non-analyte gases. The controller is further structured to measure the electrical an electrical current generated on the first and second conductive electrodes and determine the ratio of the ejected photoelectrons that are collected on the first and second conductive electrodes at the total pressure. The controller is further structured to determine an amount of electrical current due to ionization of the analyte gas by correcting the measured current using the determined ratio to remove an electrical current caused by the photoelectrons.

In an embodiment, the correcting of the measured current further comprises subtracting a fraction of the electrical current measured on the second conductive electrode from the electrical current measured on the first conductive electrode. In an embodiment, the method further includes structuring the third conductive electrode to comprise gold. In an embodiment, the method further includes structuring the second end of the chamber to be at least partially open to a surrounding environment. In an embodiment, the method further includes structuring the third conductive electrode to comprise a grid. In another embodiment, the method further includes structuring the housing to at least partially surround the radiation source. In a further embodiment, the method further includes positioning the radiation source at a first end of the chamber.

An embodiment of a method of measuring a total pressure of a gas includes structuring a photoionization sensor assembly to comprise:
(1) a housing defining a chamber including a first end and an opposing second end, wherein the chamber is permeable to molecules of the gas surrounding the housing;
(2) a radiation source structured to emit photons into the chamber;
(3) a first electrode positioned towards the first end of the chamber;
(4) a second electrode positioned in the chamber;
(5) a third electrode positioned towards the second end of the chamber; and
(6) a controller in communication with at least the first and second electrodes.

The method further includes striking the third electrode with the emitted photons to cause ejecting of photoelectron and structuring the controller to electrically bias the first, second and third conductors such that the ejected photoelectrons are attracted toward and collected on the first and second electrodes in a ratio that is dependent on a total pressure of the gas, wherein the photoelectrons generate an electrical current on the first and second electrodes. The controller is further structured to measure the electrical current generated on the first and second electrodes and determine the total pressure of the gas based on the electrical current generated on the first and second electrodes.

In an embodiment, the method further includes positioning the radiation source towards the first end of the chamber. In an embodiment, the method further includes structuring the second end of the chamber to at least be partially open to a surrounding environment. In an embodiment, the method further includes structuring the third electrode to comprise gold. In an embodiment, the method further includes structuring the housing to at least partially surround the radiation source. In another embodiment, the method further includes structuring at least one of the first, second and third electrodes to comprise a grid.

Additional features and advantages of the present disclosure are described in, and will be apparent from, the following Brief Description of the Drawings and Detailed Description.

BRIEF DESCRIPTION OF THE DRAWINGS

A more particular description of the invention briefly summarized above may be had by reference to the embodiments, some of which are illustrated in the accompanying drawings. It is to be noted, however, that the appended drawings illustrate only typical embodiments of this invention and are therefore not to be considered limiting of its scope, for the invention may admit to other equally effective embodiments. Thus, for further understanding of the nature and objects of the invention, references can be made to the following detailed description, read in connection with the drawings in which.

DETAILED DESCRIPTION

The following discussion relates to various embodiments of a data connector assembly. It will be understood that the herein described versions are examples that embody certain inventive concepts as detailed herein. To that end, other variations and modifications will be readily apparent to those of sufficient skill. In addition, certain terms are used throughout this discussion in order to provide a suitable frame of reference with regard to the accompanying drawings. These terms such as "upper", "lower", "forward", "rearward", "interior", "exterior", "front", "back", "top", "bottom", "inner". "outer", "first", "second", and the like are not intended to limit these concepts, except where so specifically indicated. The terms "about" or "approximately" as used herein may refer to a range of 80%-125% of the claimed or disclosed value. With regard to the drawings, their purpose is to depict salient features of the data connector assembly and are not specifically provided to scale.

Figure 1:
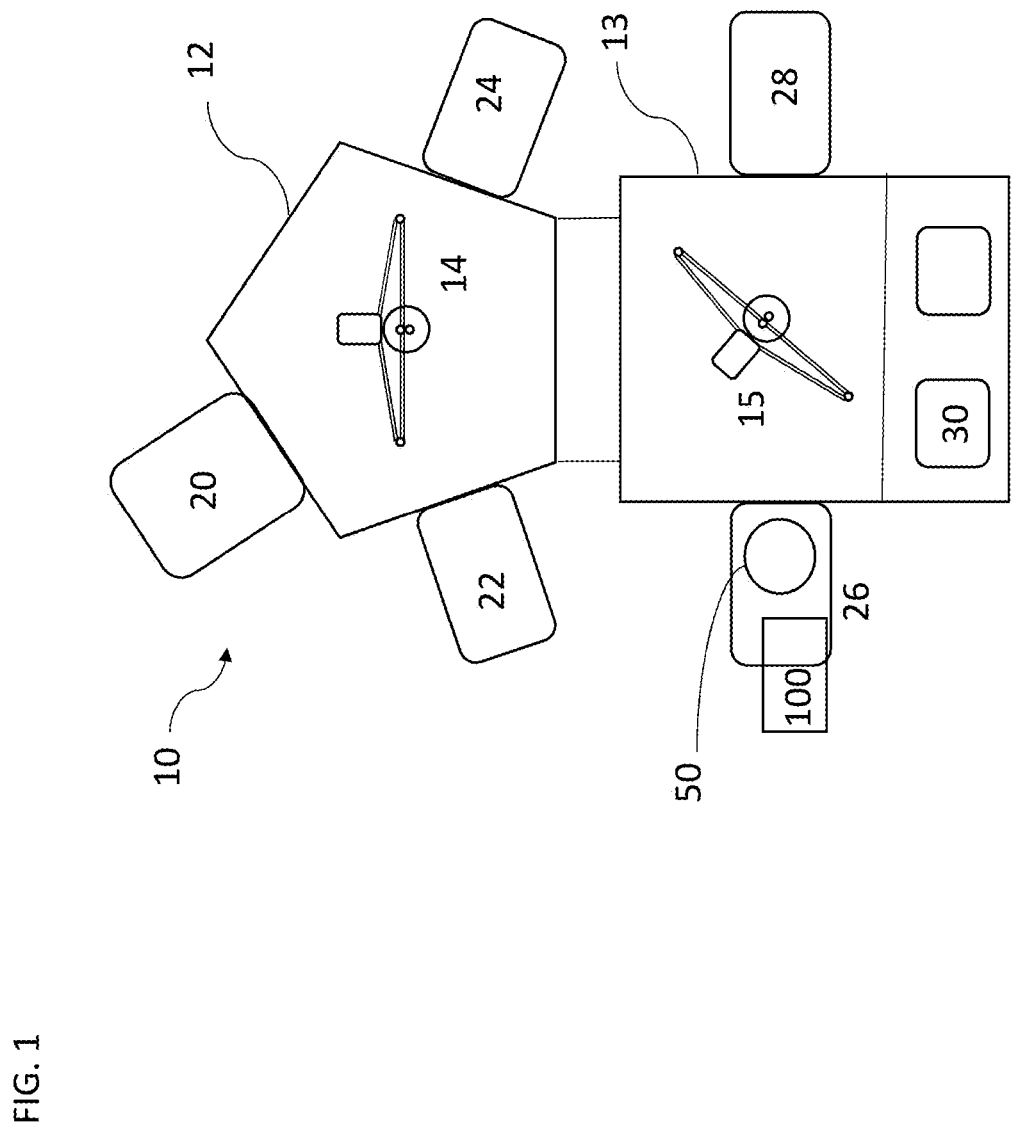
FIG. 1 schematically illustrates a sectional view of an embodiment of a cluster tool used in semiconductor fabrication.

An embodiment of a partial pressure gauge assembly for process contaminant detection using photoionization sensor gauge or gauge assembly ("sensor") 100 and an associated assembly is configured to detect the presence of hydrocarbons in the process chamber or in the semiconductor production or fabrication assembly 10, also referred to as a fabrication tool or a cluster tool, because it houses an association of chambers. In some instances, the hydrocarbon contamination occurs as a result of an incompatible component used within the fabrication of the cluster tool 10, a system leakage, or the contamination can be present on the semiconductor wafer ("wafer") 50 itself when it is introduced into tool 10. Referring to FIG. 1, the fabrication tool 10 includes a transfer module or transfer chamber 12 and a buffer module or buffer chamber 13 that are structured to house wafer processing robots 14, 15 that are capable of handling a semiconductor wafer 50. Additional process chambers 20, 22, 24, 26, 28 may be positioned around the transfer module 12 and the buffer module 13. In an embodiment, one or more of the additional process chambers 20, 22, 24, 26, 28 and capable of being open to the environment of the transfer/buffer chamber 12, 13 such that the interior environment of the additional process chambers 20, 22, 24, 26, 28 is enabled to move into the environment of the transfer/buffer chamber 12, 13 and/or the environment of the transfer/buffer chamber 12, 13 is enabled to move into the interior environment of the additional process chambers 20, 22, 24, 26, 28. After a wafer is removed from a cassette 30, it is moved through process chambers 20, 22, 24, 26, 28 which can be structured to accept the wafer as part of a fabrication step and may contain various reagents, materials, or processes that are used during one or more fabrication steps. The transfer chamber 12 and some or all of the additional process chambers 20, 22, 24, 26, 28 are maintained at a pressure that is below atmospheric pressure via a vacuum system, which may be separate from the fabrication tool 10 or may be integrated with the fabrication tool 10. A degas chamber 26 is included in the fabrication tool 10 and is configured to accept and heat the wafer 50. Heating the wafer 50 activates volatile species present on the wafer 50 such as water and hydrocarbons thus removing them from the wafer by evaporation before the fabrication process proceeds.

The sensor gauge 100 can be installed at one or more locations in the fabrication tool 10. As shown in FIG. 1, the sensor gauge 100 is installed in the degas chamber 26. A key advantage of the sensor gauge 100 is that it is able to detect the presence of an analyte, such as a hydrocarbon, determine a signal associated with that analyte, and use that signal to determine a partial pressure of the analyte. This partial pressure information can then be used in determining the completion or success of the degas process, or to detect anomalously high contamination levels which can be indicative of upstream problems in the process (e.g., photoresist removal, cleaning processes, etc.).

In the embodiment of the sensor gauge 100 shown in FIGS. 2-5, the sensor gauge 100 has a first end 111 positioned outside the process or fabrication environment and a second end 113 positioned inside the process environment. The sensor is mounted on a flange 112 that secures against an outside of the process chamber (not shown) and a sealing element 115 (e.g., a gasket or an o-ring) that creates a gas-tight seal. A support 114 is seated against an outer facing surface of the flange 112 and a wall 116 is coupled to the opposing side of the flange 112 from the support 114. As shown, the wall 116 is generally cylindrical in shape and defines a space 117. The support 114 acts to support at least two source electrodes 118 that are each positioned proximate to a radiation source 130. The source electrodes 118 could comprise metallization on the surface of the radiation source 130, conductive tapes glued to the radiation source 130, or as shown here conductive rings soldered to a circuit board 150 which is attached to support 114 by a board support 151. As shown, the radiation source 130 is a lamp having a first source end 131 that is positioned outside the process environment, and a second source end 133 that is secured inside the housing 110. The radiation source 130 surrounds a volume that is filled with a gas, such as Kr gas, however other embodiments may use a different gas. The radiation source 130 is comprised of a generally transparent material that is shatter resistant and capable of tolerating high heat and pressure variations. In an embodiment, the radiation source may be comprised or surrounded by a glass, such as Pyrex®. A seal 122 may be positioned between the flange 112 and the radiation source 130 to create a gas-tight seal. As shown this seal 122 is an o-ring with a compressive force exerted by support 114 to maintain the gas-tight seal.

Figure 4:
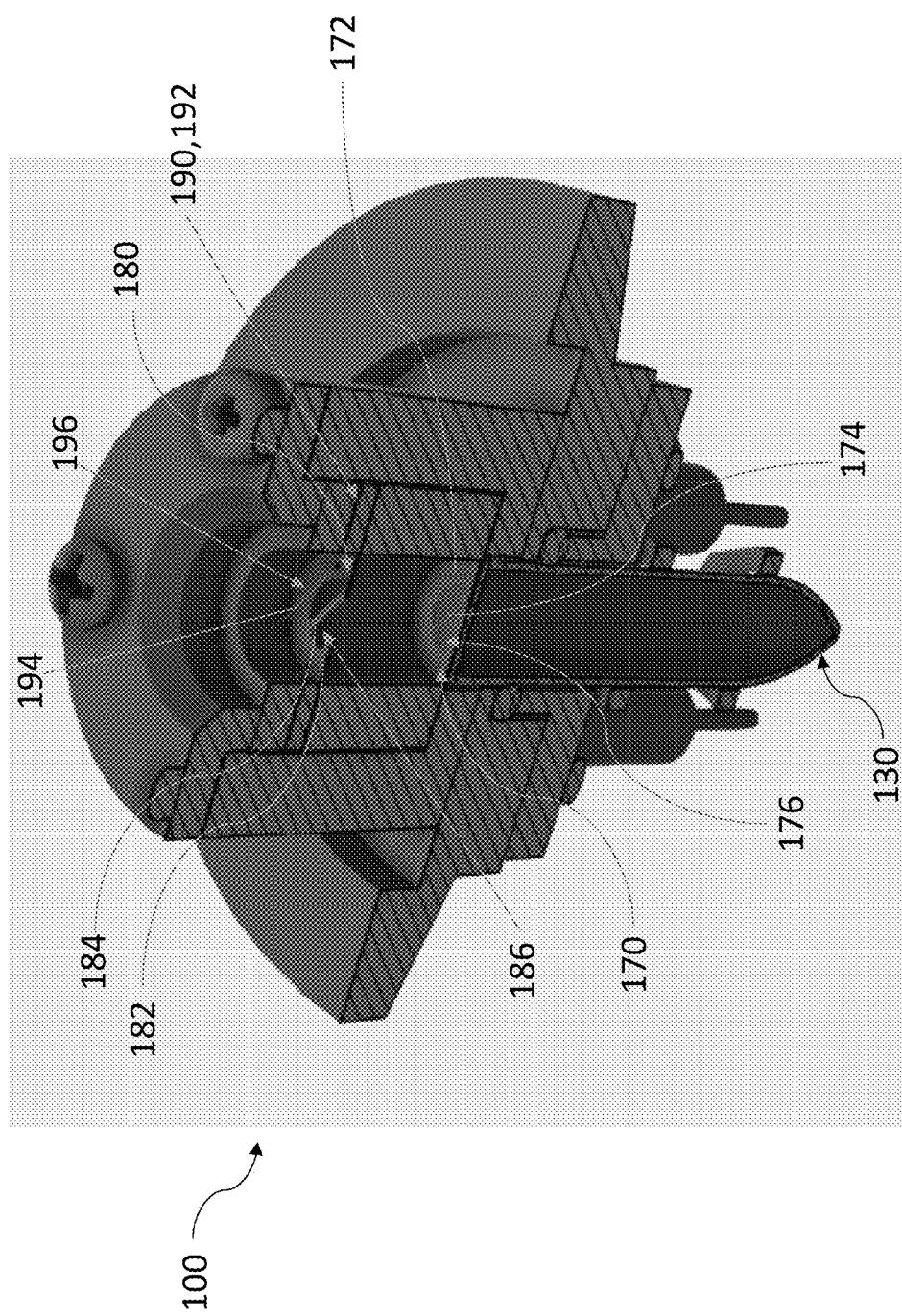
FIG. 4 illustrates a sectional view of the embodiment of the sensor gauge of FIG. 3.

The space 117 defined by the wall 116 is lined with a dielectric 160 to form an ionization chamber 162 that is bounded at a first end by a radiation window 163 that is sealed to the second source end 133 of the radiation source 130. The radiation window 163 is comprised of a UV transparent crystal that allows high energy photons to pass from the radiation source 130 into the ionization chamber 162. In some embodiments, the radiation window 163 may be comprised of magnesium fluoride, calcium fluoride, lithium fluoride or some other suitable material. A plurality of openings 164 traverse the dielectric 160 and the wall 116 to allow gases from the process chamber 189 to permeate or enter the ionization chamber 162. A first electrode 170 is positioned in the ionization chamber 162 such that the radiation window 163 is located between the second source end 133 of the radiation source 130 and the first electrode 170. As shown in the embodiment of FIG. 4, the first electrode 170 comprises a rim or outer rim 172 with one or more cross members 174 spanning the width of the outer rim 172 and/or forming a grid-like pattern. Between the cross members 174 and the outer rim 172 define a plurality of openings 176 that traverse the first electrode 170.

Figure 2:
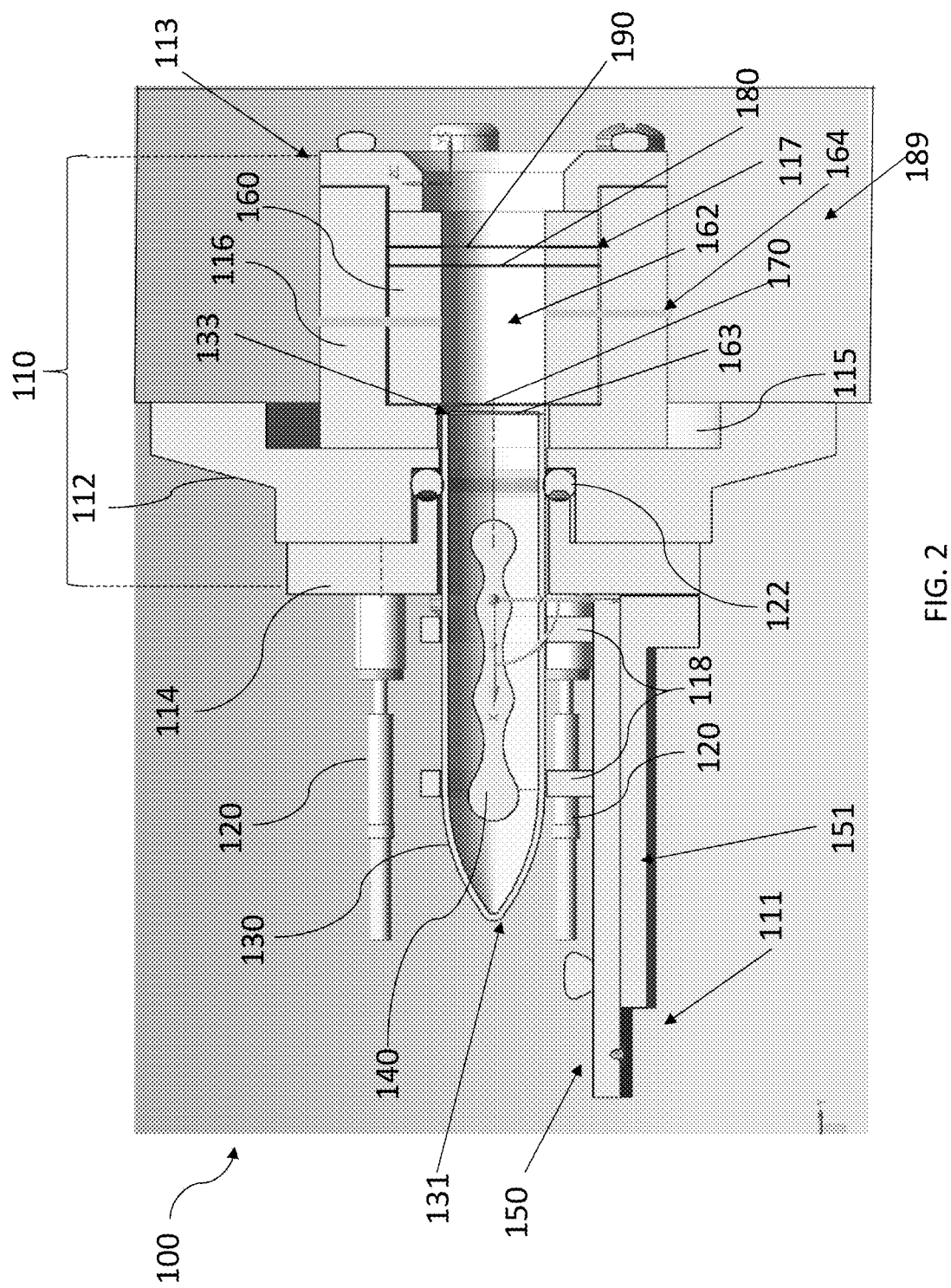
FIG. 2 illustrates a sectional view of an embodiment of a sensor gauge to be used in support of semiconductor fabrication tool.

Still referring to FIG. 4, a second electrode 180 is spaced apart from the first electrode 170 and away from the radiation window 163. The second electrode 180 comprises a rim or an outer rim 182 with one or more cross members 184 spanning the width of the rim 182 and/or forming a grid-like pattern. The rim 182 and the one or more cross members 184 define a plurality of openings 186 that traverse the second electrode 180. A third electrode 190 is spaced apart from the second electrode 180 and positioned between the second housing end 113 and the second electrode 180. Like the first and second electrodes 17, 180, the third electrode 190 comprises a rim or an outer rim 192 with one or more cross members 194 spanning the width of the rim 192 and/or forming a grid-like pattern. The rim 192 and the one or more cross members 194 define a plurality of openings 196 that traverse the third electrode 190. Electrical signals and bias voltages are provide to the first, second, and third electrodes 170, 180, 190 through the flange 112 by means of feedthroughs and conductors indicated generally by 120 (FIG. 2).

Turning back to FIG. 2, the space between the first and second electrodes 170, 180 is greater than the space between the second that third electrodes 180, 190 because the fabrication system 10 is run at low total pressures. When the pressures are low, there is a need to generate more ions in order to increase sensitivity. In an embodiment, the ratio of the space between the first and second electrodes 170, 180 to that of the space between the second and third electrode 180, 190 is 8:1. This means that a greater space between the first and second electrodes 170, 180 is needed to enable enough gas particles to enter the ionization chamber 162 for sufficient photoionization to occur. In embodiments that are used in higher pressure environments, the distance between the first and second electrodes 170, 180 can be shortened such that the ratio is less than 8:1. Although several of the embodiments show the second electrode 180 positioned between the first and third electrodes 170, 190, other embodiments may not have the second electrode 180 positioned entirely between the first and third electrodes 170, 190.

Figure 3:
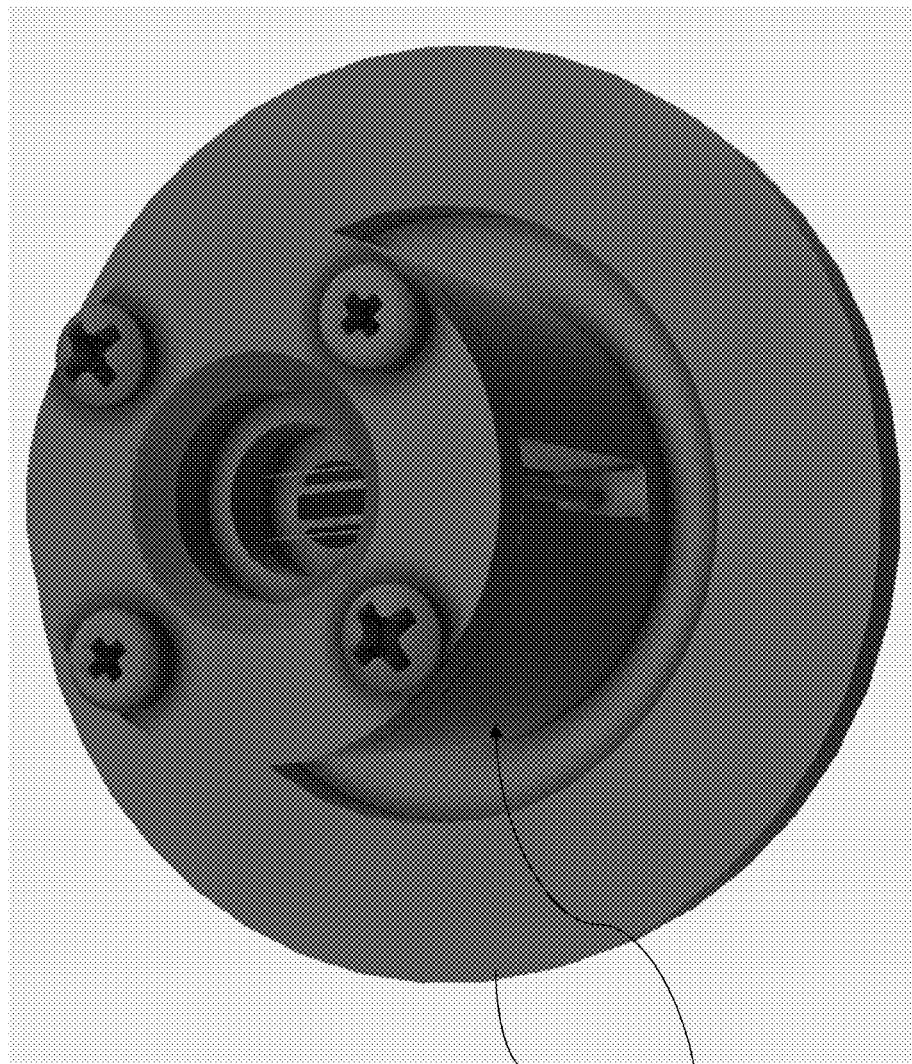
FIG. 3 illustrates a perspective view of an embodiment of the sensor gauge.
Figure 5:
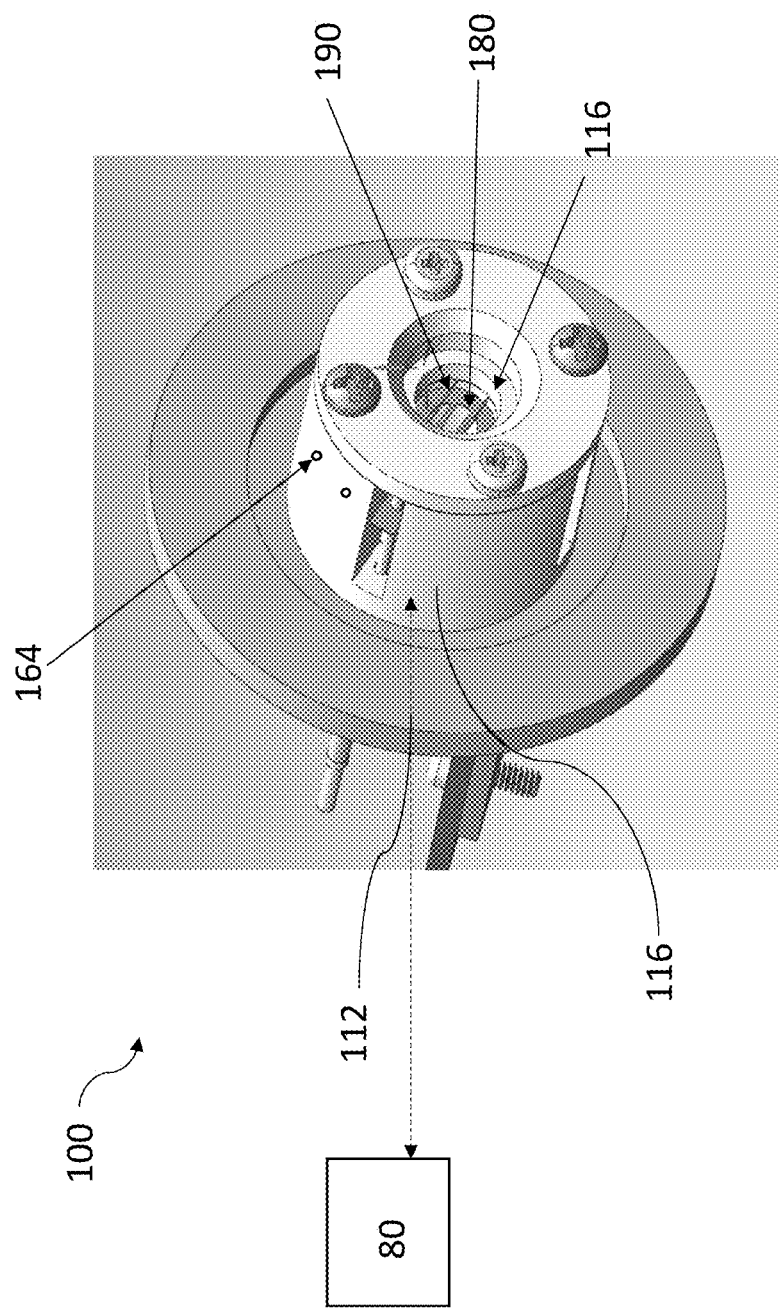
FIG. 5 illustrates a perspective view of an embodiment of the sensor gauge.

The first, second and third electrodes 170, 180, 190 are conductive and can be comprised of steel and coated with a gold plating. The gold plating does not experience a significant change in the work function when exposed to oxygen as compared to the work function of a material like stainless steel. The electrodes 170, 180, 190 are arranged in the ionization chamber 162 such their one or more cross members 174, 184, 194 shadow each other. As shown in FIGS. 3-5, each of the electrodes 170, 180, 190 have two cross members 174, 184, 194. The cross members enable the surface area of the electrodes 170, 180, 190 to be minimized in order to reduce the background noise. In other embodiments, one or more the electrodes 170, 180, 190 have more than two cross members.

The operation of the sensor part of the of the sensor gauge 100 will now be discussed with reference to FIGS. 2-5. Control electronics 80 or controller are schematically shown in FIG. 5 and are in communication with the sensor gauge 100. The control electronics 80 are typically collected together in a box that couples to the sensor flange 112, although they could be located remotely from the sensor gauge 100 and connected to the sensor gauge 100 by means of a cable. Locating the control electronics 80 in a remote location would be advantageous in instances where the sensor gauge 100 is located, for example, in an environment where the temperatures are too high for the control electronics 80 to survive. In an embodiment, the control electronics 80 may include a power supply for the radiation source 130, measurement circuits for the currents of interest, bias voltage supplies, a data processor, communications, etc. . . . . The sensor gauge 100 uses photoionization to detect the presence of an analyte in the process gas that has entered the ionization chamber 162 from the process chamber 189. The radiation source 130, in this case the lamp, is activated using the source electrodes 118 to ignite a plasma 140 within the radiation source 130. The plasma 140 emits photons through the radiation window 163 and into the ionization chamber 162. The radiation source 130 (and therefore the plasma 140) may be adjusted or controlled using a photodiode and/or camera to measure fluctuations of the light being emitted by the plasma 140. The radiation source 130 can accordingly be fine-tuned to eliminate such fluctuations. At least some of the photons are of a wavelength that is capable of ionizing molecules of the analyte gas in the ionization chamber 162, for example molecules of hydrocarbon gas. When the photons collide with the molecules of the analyte gas, they have enough energy to produce ions from the analyte gas molecules by ejecting an electron.

The first, second and third electrodes 170, 180, 190 are biased to dictate the flow of one or more of the charged particles in the ionization volume 162. In an example, the first electrode 170 and the second electrode 180 are held at virtual ground through current-to-voltage converting amplifiers (I-to-V) and the third electrode 190 acts as a cathode held at some negative potential with respect to ground, typically between −80V and −300V. Photons are emitted by the radiation source 130 and travel through the radiation window 163 into the ionization volume 162 where they collide with analyte gas molecules. In an embodiment, the radiation source 130 is positioned towards an end of the ionization volume 162. Each collision has some probability of causing ejection of an electron from the analyte gas molecule creating a positive ion that moves towards the cathode/third electrode 190 while the ejected electron moves towards the first electrode 170 or the second electrode 180, depending on where the ionization takes place, the sensor geometry, bias voltage, and/or the pressure of the background gas. The wavelength of the some of the photons is short enough to efficiently ionize most organic molecules, but the photons are not sufficiently energetic to ionize the background gas, typically nitrogen or argon or hydrogen, which may be present in the ionization chamber 162.

The electron currents collected at the first electrode 170 and second electrode 180 are transported by means of the feedthroughs 120 (see FIG. 2) to the control electronics 80 where the currents are converted to voltages, amplified, and digitized. The presence of an electron current as detected by the controller 80 is an indication that the analyte gas may be present in the process chamber 189. In addition to this electron current produced by the photoionization of the analyte gas molecules, another source of electron current can be measured by the sensor gauge 100. Photons that are energetic enough to ionize hydrocarbons for example, have more than enough energy to cause electrons to be ejected from most conductors (photoelectrons). Photoelectrons generated at the third electrode 190 surface are accelerated toward the first and second electrodes 170, 180 by the electric field established by the third electrode 190 bias and collected, causing a baseline current on these electrodes and contributing whatever noise and drift exist on this photoelectron current to the measured signals of interest. If these photoelectron currents were constant they could just be subtracted from the signal, but they are not generally constant. Therefore, reducing both the noise and drift on the photoelectron current improves the sensor gauge's 100 ability to measure hydrocarbons. One way to reduce absolute noise and drift is to reduce the photoelectron current as a whole. This can be done by reducing the area of the third electrode 190 that is exposed to the UV photons. By reducing the exposed area of the third electrode or third electrode 190 that is acting as a source of photoelectrons, one can reduce the photoelectron current as well as the absolute noise on this current. The embodiment of the sensor gauge 100 shown in the figures has a third electrode 190 comprising two gold wires that are 0.75 mm in diameter and stretched across the third electrode diameter to provide the required electric field while minimizing the photoelectron-producing area as far as was found practical.

Figure 11:
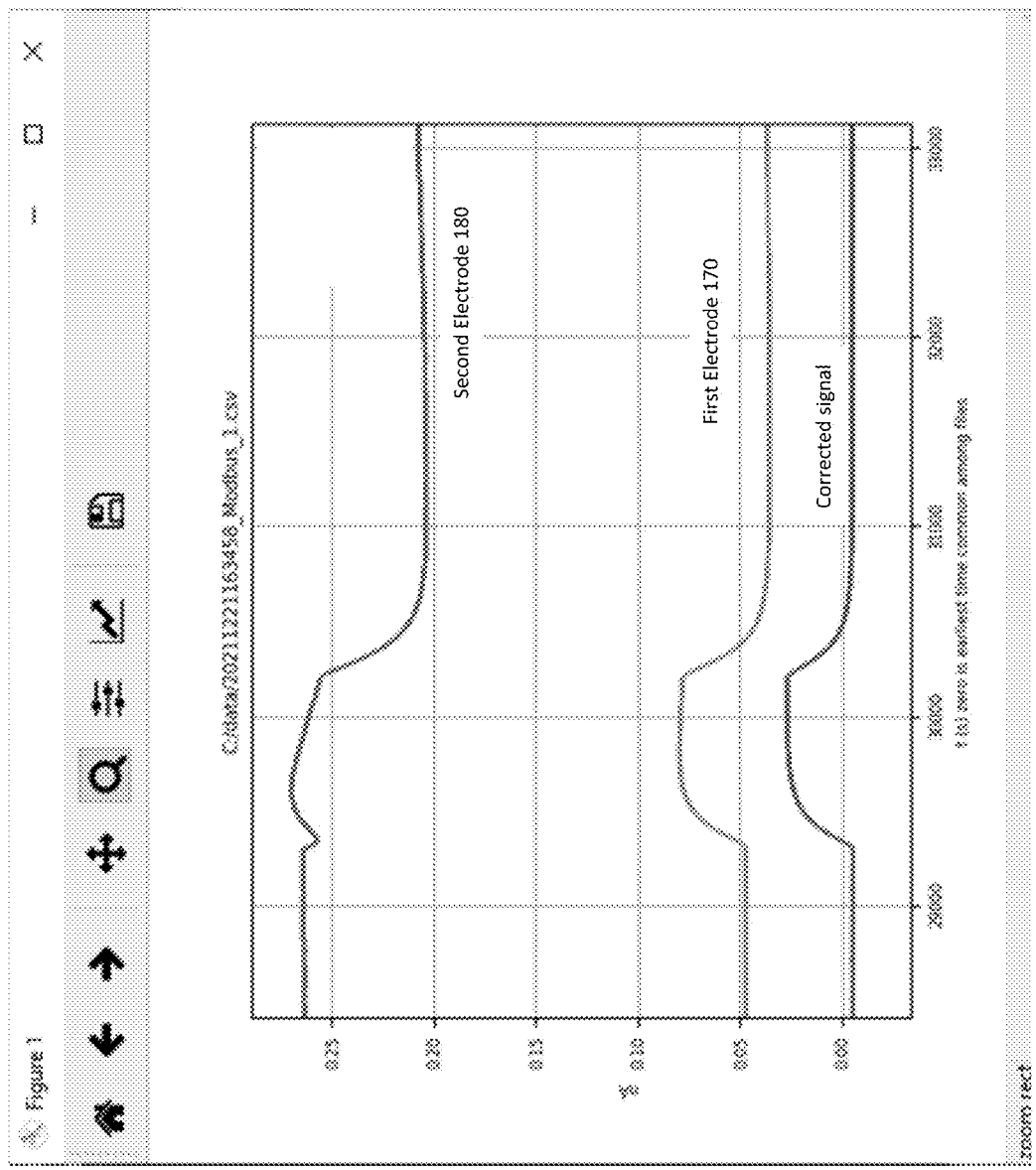
FIG. 11 illustrates effectiveness of correction for photoelectron currents.

Furthermore, the photoelectron current produced for a given photon flux and energy profile depends on the work function of the illuminated surface. If this work function is not constant, then the current that is produced will not be constant, even given all other variables (photon flux, area, temperature) being fixed. The work function of a conductive surface can be affected by the presence of water or oxygen, or other highly electronegative chemicals as may be present in certain wafer etch environments. These effects on signal currents are relevant to the monitoring of hydrocarbon contaminants in certain semiconductor processes when for example a wafer may be transferred from an environment with oxygen to one without. Remaining effects on background photoelectron currents can mask small hydrocarbon signals of interest. FIG. 11 illustrates this effect and one way to overcome it in this sensor gauge 100. Here, a square pulse of 10 ppm of isobutylene is injected into a balance of nitrogen from 29300 seconds to 30200 seconds while keeping the total pressure constant. Before and after the pulse, the sensor gauge 100 was exposed to pure nitrogen, but during the pulse, in addition to the isobutylene, the oxygen concentration was increased from zero to 1%. In comparing the signals before and after the pulse on the first and second electrodes 170, 180, a shift in the baseline is discernable. This shift in the baseline results from a decrease in the photoelectron production that takes place during and continues after the sample pulse because the sensor 100 was exposed to oxygen The baseline recovers only very slowly afterwards. This effect is due to the work function of the (mainly) third electrode 190 surface. In order to get a stable baseline relative to which the hydrocarbon pulse can be measured, one can subtract the photoelectron fraction of the signal measured on the second electrode 180 from that measured on the first electrode 170. When this fraction is chosen correctly, it removes that photoelectron effects from the data, as shown in the "corrected signal" on FIG. 11.

Figures 6A, 6B:
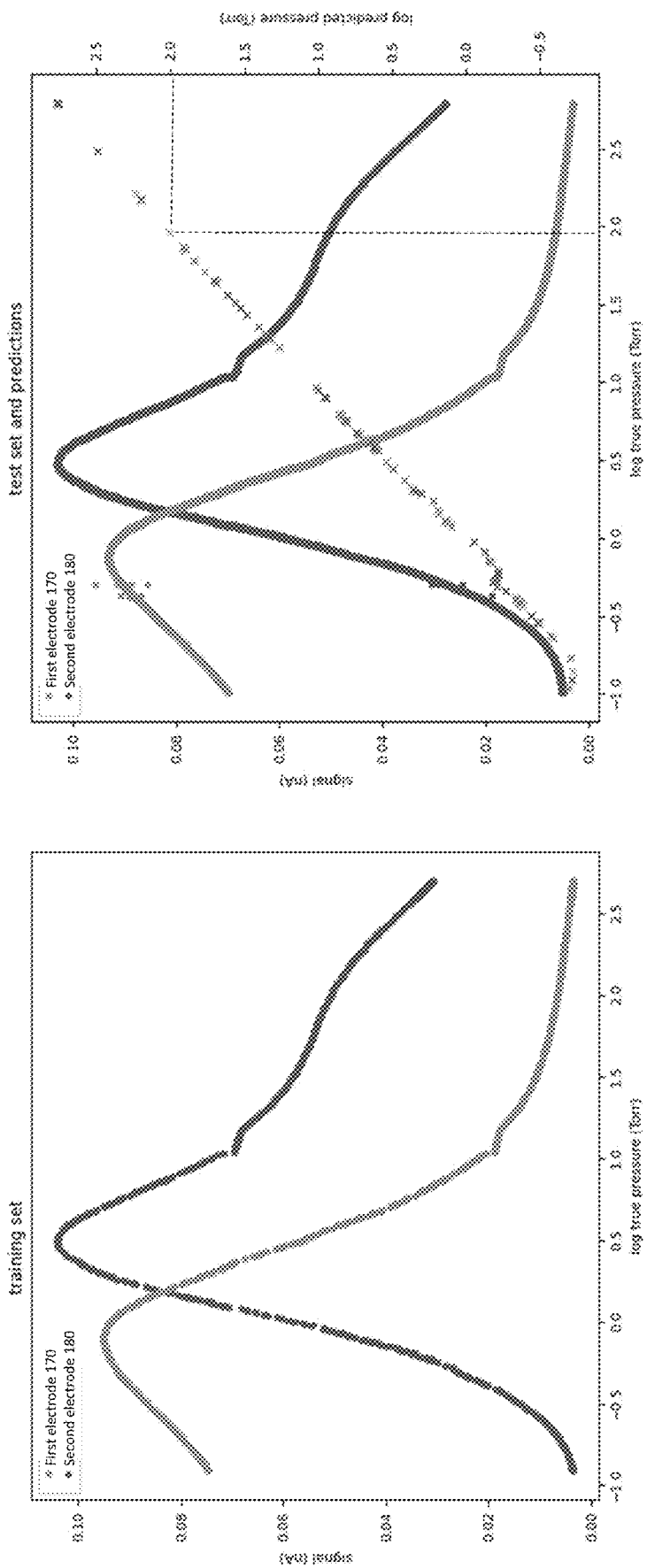
FIG. 6 illustrates examples of predicting total pressure based on a regression model of photoelectron currents in the sensor gauge.

The distribution of these photoelectrons on the first and second electrodes 170, 180 is a fairly complicated function of the pressure at which the sensor 100 is being operated. FIG. 6a shows the photoelectron currents measured on the first and second electrodes 170, 180 as a function of pressure in nitrogen with a third electrode 190 bias of −80 V. The shapes of these curves is due to pressure-dependent scattering of photoelectrons off of the background gas. The correct fraction of second electrode signal to subtract from the first electrode signal to derive the "corrected" signal can be read from a plot like this for the pressure of interest. Once these two curves have been determined for a particular electrode geometry, the pressure in the sensor 100 can be determined from the two electrode signals for a period of a process where there are not expected to be hydrocarbon signals present, such as before turning on the heat in a wafer degas process. As an illustration, a regression model of pressure was created for the two electrode signals in the training set of data depicted in FIG. 6a. A standard machine learning algorithm based on kernel ridge regression was used to develop a model that predicts pressure based on the two currents. This model was then applied to the two sensor currents in a separate test data set shown in FIG. 6b. This data in 6b was not used for training the model. For a random set of current measurements, the "predicted pressure" was found. This predicted pressure is displayed on the second y-axis. An example is shown with a dotted line, where the two currents measured at ~195 Torr were used to predict a pressure of ~198 Torr. In this way, the sensor 100 can not only be used to measure hydrocarbon partial pressures, but also to measure the total pressure in the system, even when the major species cannot be ionized by the UV photons.

Of course, if one were to optimize for total pressure measurement rather than for the measurement of species ionized by the UV photons, then one would not necessarily try to minimize photoelectron production area as is done in the disclosed sensor 100. And it may also be desirable to use a light source where the energy is sufficient to make photoelectrons from the third electrodes or cathodes, but where the energy is too low to ionize hydrocarbons or other gaseous species.

The calculations for "corrected signals" and "predicted pressure" can be performed by an on-board processor in the control electronics 80, or by a remote computer.

Another way to reduce these photoelectron effects is to stabilize the photoelectron production against work function changes. As the work functions of some conductive surfaces are more strongly affected by the presence of oxygen and/or water on them than are others, choosing the third electrode surface material carefully can help. Gold is less susceptible to this effect than stainless steel, so the third electrode 190 of the sensor 100 described herein has a gold surface. This has been realized in different ways; e.g., with gold wires and gold plated stainless parts. The first and second electrodes 170, 180 can also be gold plated, but these surfaces are not as important since the typical biasing in the sensor helps to prevent photoelectron currents from originating at these surfaces and being collected elsewhere.

Figure 7:
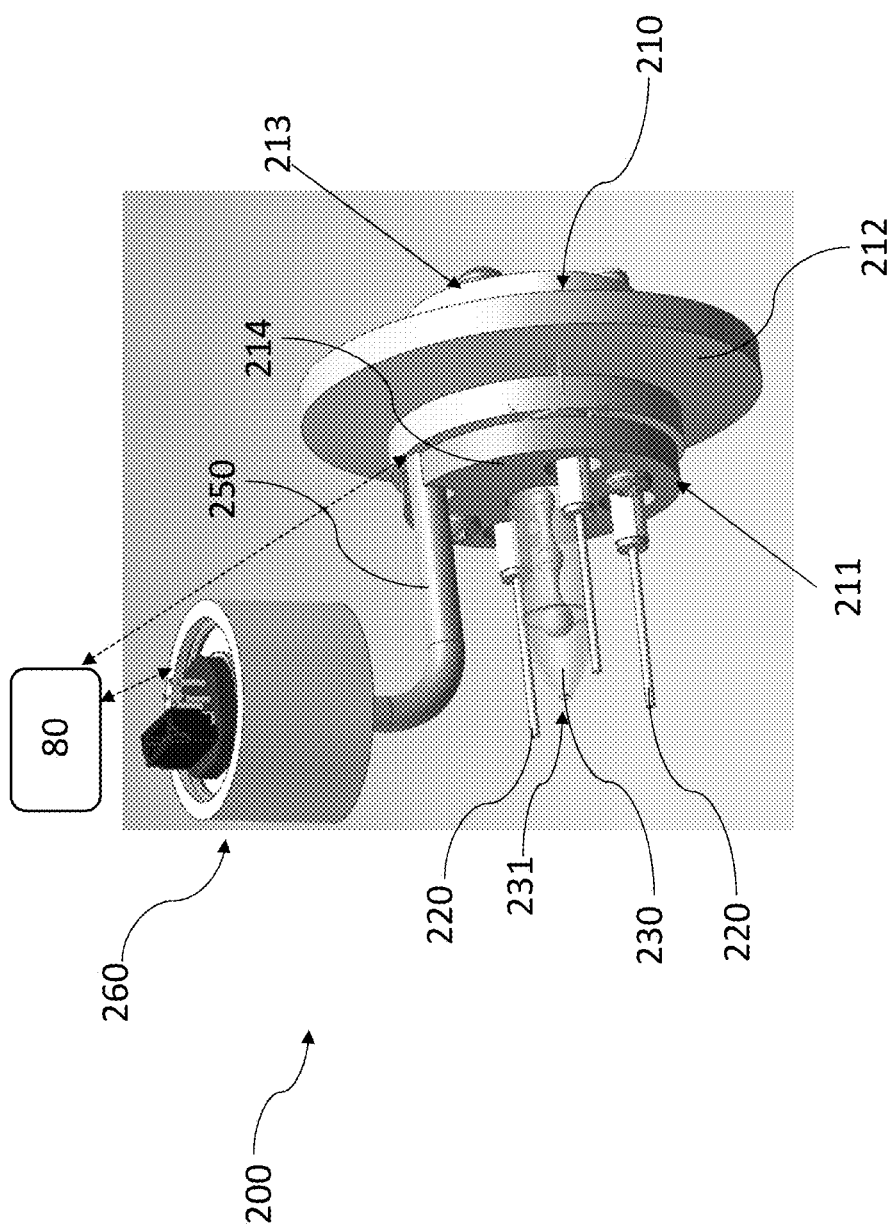
FIG. 7 illustrates a perspective view of another embodiment of the sensor gauge.

Referring to FIG. 7, another embodiment of the sensor gauge 200 is shown. This embodiment is the same as that described above except for the addition of an integral total pressure gauge 260. In this embodiment, the sensor gauge 200 comprises a sensor portion 210 and a pressure gauge portion 260. The sensor portion 210 includes a first end 211 and a second end 213. A flange 212 or other surface that is configured to be attached to a part of the process chamber or other support is provided. A support 214 is located on one side of the flange 212 and is structured to support one or more electrodes (not shown) positioned proximate a radiation source 230. The one or more electrodes are not shown, but may be similar to other embodiments of the electrodes previously discussed. Similar to the embodiments previously discussed, a wall is coupled to the opposing side of the flange 212 relative to the support 214 and defining a space. As shown in FIG. 7 and as described in other embodiments, the radiation source 230 is a lamp. The radiation source 230 has a first source end 231 that is positioned outside, and a second source end that is secured inside. One or more feedthroughs 220 may connect to or communication with a power supply or the controller 80. As shown, the radiation source 230 surrounds a volume that is filled with a gas, such as Kr gas, however other embodiments may use a different gas. The radiation source 230 is comprised of a generally transparent material that is shatter resistant and capable of tolerating high heat and pressure variations. In an embodiment, the radiation source 230 is comprised of a glass, such as Pyrex®.

A tube 250 pneumatically couples the atmosphere in which the sensor gauge 200 is mounted to a pressure gauge 260. The pressure gauge 260 is chosen to measure pressures in the range at which the sensor is intended to be operated. Including the pressure gauge 260 with the sensor gauge 200 can save a flange on the process system being monitored. The pressure inside of the ionization chamber is measured by the pressure gauge 260 can also be used for making the photoelectron corrections described above. Measurements of the pressure and of the photoelectron current on the second electrode, and knowledge of how the ratio of the photoelectron currents measured on the first and second electrodes depends on pressure allows for removal of the photoelectron contribution to the current measured on the first electrode, leaving the corrected analyte signal. The pressure measurements are reported to the control electronics 80 where they are used, logged, and/or passed on to the sensor's user. The wall has an inner space lined with a dielectric to define an ionization space similar to embodiments previously discussed. Three electrodes (not shown) are positioned in the ionization space. A first electrode (not shown) is positioned proximate the radiation window (not shown) followed by the second and third electrode (not shown) and spaced apart from each other such that the second electrode (not shown) is positioned between the first electrode (not shown) and the third electrode (not shown). The electrodes (not shown) are configured in a similar manner to the first, second and third electrodes 170, 180, 190 previously discussed. One or more openings (not shown) may be defined in the wall and the dielectric to enable gases from the process chamber to enter into the ionization chamber (not shown). Detection of the analyte and the pressure determination proceeds in a similar manner as that described in the previous embodiments.

Figure 8:
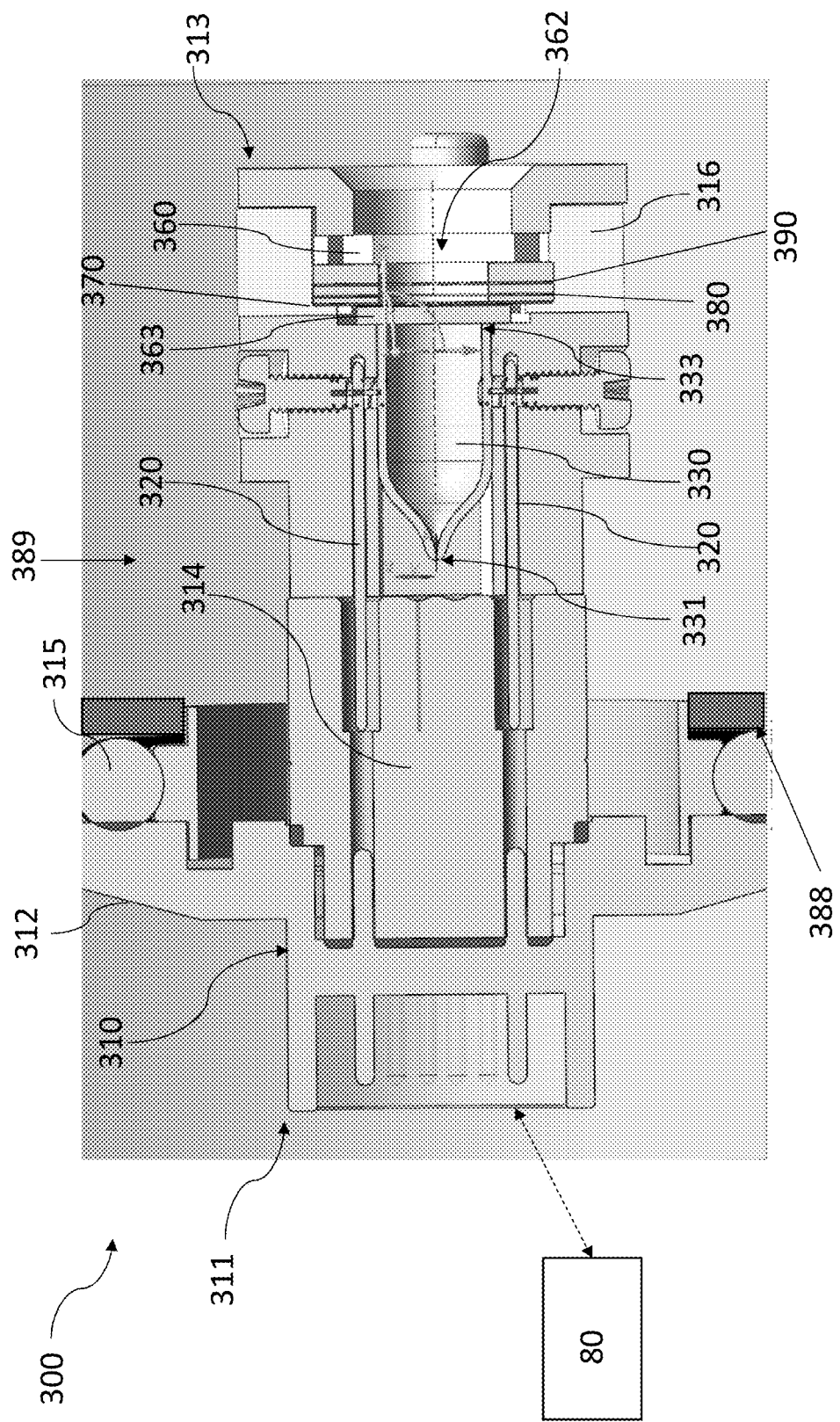
FIG. 8 illustrates a sectional view of another embodiment of the sensor gauge.
Figure 9:
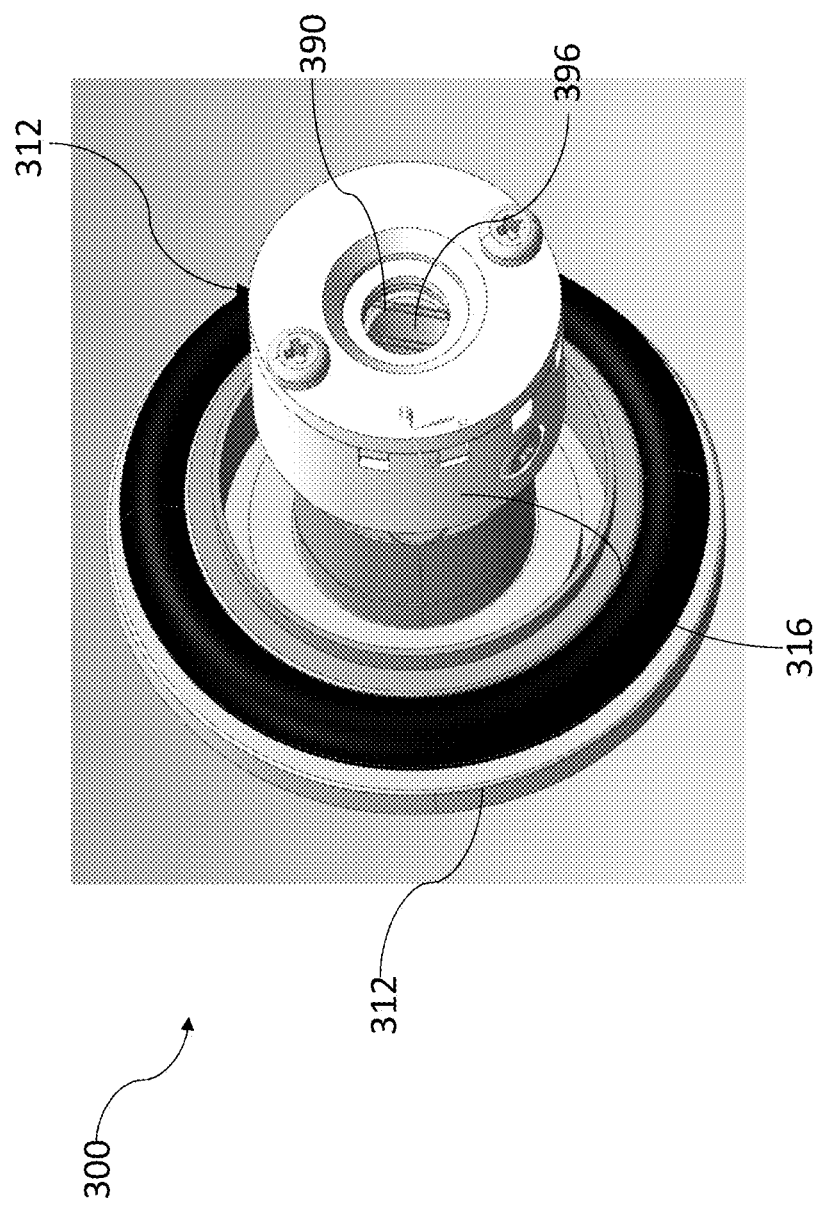
FIG. 9 illustrates a perspective view of the embodiment of FIG. 8.
Figure 10:
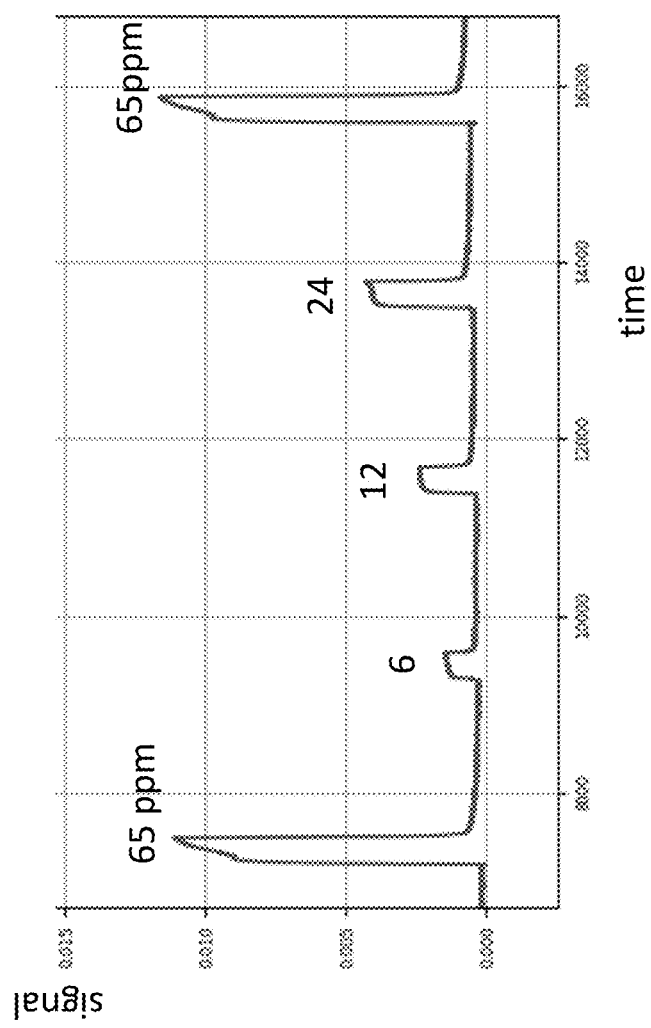
FIG. 10 is an example of photoelectron-current corrected measurements of xylene pulses of various concentrations using the sensor.

Referring to FIGS. 8 and 9, another embodiment of a sensor gauge 300 is shown and will now be described. This embodiment of the sensor gauge 300 positions the radiation source 330 completely inside the process chamber 389 such that the sensor gauge 300 can be positioned in close proximity to the wafer 50 being processed or any other portion of the fabrication assembly 10. The sensor gauge 300 has a multi-pin vacuum feedthrough assembly 310 including a first side 311 that is positioned outside the process or fabrication environment and a second side 313 positioned inside the process environment. The multi-pin vacuum feedthrough assembly 310 has a flange 312 that secures against an outside 388 of the process chamber 389 and a sealing element 315 that creates a gas-tight seal. A support 314 is positioned inside the multi-pin vacuum feedthrough assembly 310. A housing wall 316 extends in a direction away from the flange 312 and comprises a generally cylindrical in shape that defines a space. The support 314 acts to support at least two electrodes 320 that are each positioned proximate to a radiation source 330. As shown, the radiation source 330 is again a lamp. The radiation source 330 includes a first source end 331, and a second source end 333 that is secured inside the housing 316 on the process side of the flange 312. The radiation source 330 surrounds a volume that is filled with a gas, such as Kr gas, however other embodiments may use a different gas. The radiation source 330 is comprised of a generally transparent material that is shatter resistant and capable of tolerating high heat and pressure variations. In an embodiment, the radiation source is comprised of or surrounded by a glass, such as Pyrex®. In an embodiment, housing wall 316 serves as a sleeve to at least partially surrounds the radiation source 330 and encapsulate the electrodes that drive the radiation source 330. The housing wall 316 is ideally made of Teflon® or other similar fluoropolymer as a reasonable choice for vacuum and process compatibility and high breakdown voltage. This dielectric barrier serves to prevent discharges from the source electrodes that can occur at some sensor operating pressures and transient pressures likely to be experienced in use. In other embodiments, the radiation source 330 is potted in general with the exception of the radiation window 363.

The space defined by the wall 316 is lined with a dielectric 360 to form an ionization space or an ionization chamber 362 that is bounded at a first end by a radiation window 363 that is sealed to the second source end 333 of the radiation source 330. A plurality of openings may traverse the dielectric 360 and the wall 316 to enable gases from the process chamber to enter the ionization chamber 362. The opposing end of the ionization chamber 362 is also open to the process chamber 389 as in previously discussed embodiments of the sensor gauge 100, 200. A first electrode 370 is positioned in the ionization chamber 362 such that the radiation window 363 is located between the second source end 333 of the radiation source 330 and the first electrode 370. In the illustrated embodiments, a second electrode 380 is positioned in the ionization space 362 spaced apart from the first electrode 370 such that the first electrode 370 is generally positioned between the radiation window 363 and the second electrode 380. A third electrode 390 is positioned apart from the second electrode 380 and towards opposing end of the ionization chamber 362. The first, second and third electrodes 370, 380, 390 are positioned similar to other embodiments previously discussed and may also be structured in a similar manner to other embodiments previously discussed. In the embodiment shown in FIG. 9, the third electrode 390 is particularly shown and defines a series of circular openings 396 that traverse the third electrode 390, however the third electrode 390 may be configured as in previously described embodiments for the reasons previously explained. Detection of the analyte gas molecules and the pressure determination proceeds in a similar manner as that described in the previous embodiments. Electrical connections to the control electronics 80 from the sensor are made via the pins in feedthrough assembly 310.

While the present invention has been particularly shown and described with reference to certain exemplary embodiments, it will be understood by one skilled in the art that various changes in detail may be effected therein without departing from the spirit and scope of the invention that can be supported by the written description and drawings. For example, the disclosed method and assembly may be used to determine analyte number density or other properties of a sample in the sensor chamber. Further, where exemplary embodiments are described with reference to a certain number of elements, it will be understood that the exemplary embodiments can be practiced utilizing either less than or more than the certain number of elements.

What is claimed is:

1. A sensor assembly for measuring a total pressure of a gas, comprising:
   a housing defining a chamber including a first end and an opposing second end, wherein the chamber is permeable to molecules of the gas surrounding the housing;
   a radiation source configured to emit photons into the chamber;

a first electrode positioned towards the first end of the chamber;
a second electrode positioned in the chamber;
a third electrode positioned towards the second end of the chamber; and
a controller in communication with at least the first and second electrodes,
wherein the photons emitted into the chamber cause an ejection of photoelectrons from the third electrode;
wherein the controller is configured to,
electrically bias the first, second and third electrodes such that the ejected photoelectrons are attracted toward and collected on the first and second electrodes in a ratio that is dependent on a total pressure of the gas, wherein the photoelectrons generate an electrical current on the first and second electrodes,
measure the electrical current generated on the first and second electrodes, and
determine the total pressure of the gas based on the electrical current generated on the first and second electrodes.

2. A sensor assembly of claim 1, wherein the radiation source is positioned towards the first end of the chamber.

3. The sensor assembly of claim 1, wherein the second end of the chamber is at least partially open to a surrounding environment.

4. The sensor assembly of claim 1, wherein the third electrode comprises gold.

5. The sensor assembly of claim 1, wherein the radiation source is at least partially surrounded by the housing.

6. The sensor assembly of claim 1, wherein a ratio of a distance between the first and second electrodes to that of a distance between the second and third electrodes is about 8:1.

7. The sensor assembly of claim 1, wherein at least one of the first, second and third electrodes comprises a grid.

8. A photoionization sensor assembly configured to measure an analyte gas in a presence of non-analyte gases, comprising:
a housing defining a chamber with a first end and an opposing second end, wherein the chamber is permeable to molecules of the analyte gas and non-analyte gases surrounding the housing;
a radiation source configured to emit photons into the chamber;
a first conductive electrode positioned towards the first end of the chamber;
a second conductive electrode positioned in the chamber;
a third conductive electrode positioned towards the second end of the chamber; and
a controller in communication with at least the first and second conductive electrodes,
wherein the emitted photons ionize at least some molecules of the analyte gas, wherein the emitted photons are insufficient to ionize molecules of the non-analyte gases,
wherein the emitted photons strike the third conductive electrode resulting in ejection of photoelectrons,
wherein the controller is configured to:
receive a measurement of a total pressure of the analyte gas and the non-analyte gases,
electrically bias the first, second and third conductive electrodes such that the photoelectrons are attracted toward and collected on the first and second conductive electrodes in a ratio that is dependent on the total pressure of the analyte gas and the non-analyte gases,
measure an electrical current generated on the first and second conductive electrodes,
determine the ratio of the ejected photoelectrons that are collected on the first and second conductive electrodes at the total pressure, and
determine an amount of electrical current due to ionization of the analyte gas by correcting the measured current using the determined ratio to subtract an electrical current caused by the photoelectrons from the measured electrical current.

9. The photoionization sensor of claim 8, wherein the correcting of the measured current further comprises subtracting a fraction of the electrical current measured on the second conductive electrode from the electrical current measured on the first conductive electrode.

10. The photoionization sensor of claim 8, further comprising a pressure gauge mounted on a flange and configured to measure a total pressure and provide the measured total pressure to the controller.

11. The photoionization sensor of claim 8, wherein the second end of the chamber is at least partially open to a surrounding environment.

12. The photoionization sensor of claim 8, wherein the third conductive electrode comprises gold.

13. The photoionization sensor of claim 8, wherein the radiation source is at least partially surrounded by the housing.

14. The photoionization sensor of claim 8, further comprising locating the radiation source at the first end of the chamber.

15. A method for measuring an analyte gas in a presence of non-analyte gases, comprising:
structuring a photoionization sensor to comprise,
a housing defining a chamber with a first end and an opposing second end, wherein the chamber is permeable to molecules of the analyte gas and non-analyte gas surrounding the housing;
a radiation source configured to emit photons;
a first conductive electrode positioned towards the first end of the chamber;
a second conductive electrode positioned in the chamber;
a third conductive electrode positioned towards the second end of the chamber; and
a controller in communication with at least the first and second conductive electrode,
emitting photons from the radiation source into the chamber to ionize at least some molecules of the analyte gas, wherein the emitted photons are insufficient to ionize molecules of the non-analyte gases,
emitting photons from the radiation source into the chamber to strike the third conductive electrode and cause an ejection of photoelectrons,
wherein the controller:
receives a measurement of a total pressure of the analyte gas and the non-analyte gases,
electrically biases the first, second and third conductive electrodes such that the photoelectrons are attracted toward and collected on the first and second conductive electrodes in a ratio that is dependent on the total pressure of the analyte gas and the non-analyte gases,
measures an electrical current generated on the first and second conductive electrodes,
determines the ratio of the ejected photoelectrons that are collected on the first and second conductive electrodes at the total pressure, and determines an amount of electrical current due to ionization of the analyte gas by correcting the measured current using the determined ratio to remove an electrical current caused by the photoelectrons.

16. The method of claim 15, further including structuring the third conductive electrode to comprise gold.

17. The method of claim 15, further including structuring the second end of the chamber to be at least partially open to a surrounding environment.

18. The method of claim 15, further including structuring the third conductive electrode to comprise a grid.

19. The method of claim 15, further including structuring the housing to at least partially surround the radiation source.

20. The method of claim 15, further including positioning the radiation source at a first end of the chamber.

21. A method of measuring a total pressure of a gas, comprising:
   structuring a photoionization sensor assembly to comprise, a housing defining a chamber including a first end and an opposing second end,
   wherein the chamber is permeable to molecules of the gas surrounding the housing,
      a radiation source configured to emit photons into the chamber,
      a first electrode positioned towards the first end of the chamber,
      a second electrode positioned in the chamber,
      a third electrode positioned towards the second end of the chamber, and
      a controller in communication with at least the first and second electrodes;
   striking the third electrode with the emitted photons to cause ejecting of photoelectrons; and
   wherein the controller:
      electrically biases the first, second and third conductors such that the ejected photoelectrons are attracted toward and collected on the first and second electrodes in a ratio that is dependent on a total pressure of the gas, wherein the photoelectrons generate an electrical current on the first and second electrodes,
      measures the electrical current generated on the first and second electrodes, and
      determines the total pressure of the gas based on the electrical current generated on the first and second electrodes.

22. The method of claim 21, further comprising positioning the radiation source towards the first end of the chamber.

23. The method of claim 21, further comprising structuring the second end of the chamber to at least be partially open to a surrounding environment.

24. The method of claim 21, further comprising structuring the third electrode to comprise gold.

25. The method of claim 21, further comprising structuring the housing to at least partially surround the radiation source.

26. The method of claim 21, further comprising structuring at least one of the first, second and third electrodes to comprise a grid.

* * * * *

UNITED STATES PATENT AND TRADEMARK OFFICE
CERTIFICATE OF CORRECTION

PATENT NO. : 12,203,887 B2
APPLICATION NO. : 18/286627
DATED : January 21, 2025
INVENTOR(S) : Shawn M. Briglin, Michael F. Vollero and John Gordon Wiley Page 1 of 1

It is certified that error appears in the above-identified patent and that said Letters Patent is hereby corrected as shown below:

On the Title Page

Item (71) Applicant should read as follows: INFICON, INC.

Item (22) PCT Filed should read as follows: April 19, 2023

Item (83) PCT No. should read as follows: PCT/US2023/019041

Item (87) PCT Pub. No. should read as follows: WO2023/205198

Signed and Sealed this
Twenty-seventh Day of May, 2025

Coke Morgan Stewart
*Acting Director of the United States Patent and Trademark Office*